United States Patent
Hines (10) Patent No.: US 7,500,379 B2
(45) Date of Patent: Mar. 10, 2009

(54) ACOUSTIC WAVE ARRAY CHEMICAL AND BIOLOGICAL SENSOR

(75) Inventor: Jacqueline H. Hines, Annapolis, MD (US)

(73) Assignee: Applied Sensor Research & Development Corporation, Arnold, MD (US)

(*) Notice: Subject to any disclaimer, the term of this patent is extended or adjusted under 35 U.S.C. 154(b) by 125 days.

(21) Appl. No.: 11/768,736

(22) Filed: Jun. 26, 2007

(65) Prior Publication Data

US 2008/0156100 A1   Jul. 3, 2008

Related U.S. Application Data

(60) Provisional application No. 60/816,464, filed on Jun. 26, 2006.

(51) Int. Cl.
  *G01N 29/036* (2006.01)
  *H01L 41/08* (2006.01)
(52) U.S. Cl. .................. 73/24.06; 73/24.01; 73/61.75; 73/64.53; 310/313 D; 310/313 B; 310/313 R
(58) Field of Classification Search .............. 73/24.06, 73/24.01, 61.75, 64.53; 310/313 D, 313 B, 310/313 R
See application file for complete search history.

(56) References Cited

U.S. PATENT DOCUMENTS

| | | | |
|---|---|---|---|
| 6,235,471 B1* | 5/2001 | Knapp et al. | 435/6 |
| 6,571,638 B2 | 6/2003 | Hines et al. | |
| 6,907,787 B2 | 6/2005 | Cook et al. | |
| 7,015,030 B1* | 3/2006 | Fouillet et al. | 435/287.1 |
| 7,389,673 B2* | 6/2008 | Kimura et al. | 73/24.06 |
| 7,437,907 B2* | 10/2008 | Kimura et al. | 73/24.06 |
| 2001/0055529 A1* | 12/2001 | Wixforth | 417/53 |
| 2005/0056098 A1 | 3/2005 | Solie | |

(Continued)

OTHER PUBLICATIONS

A Novel Love-Plate Acoustic Sensor Utilizing Polymer Overlayers—Lowe et al IEEE Transactions On Ultrasonics, Ferroelectrics, and Frequency Control, vol. 39, No. 5, Sep. 1992—pp. 657-659.

(Continued)

*Primary Examiner*—Hezron Williams
*Assistant Examiner*—Rose M Miller
(74) *Attorney, Agent, or Firm*—Schiff Hardin LLP (57) ABSTRACT

An acoustic wave sensor array device is provided for the detection, identification, and quantification of chemicals and biological elements dispersed in fluids. The sensor array device is capable of the simultaneous characterization of a fluid for multiple analytes of interest. A substrate has a plurality of channels formed therein and a sensor material layer applied in a bottom of the channels. The sensor material layer has a shear acoustic wave speed lower than a shear acoustic wave speed in said substrate. The channels may have the same material in each channel or different materials in at least two of the channels. A surface acoustic wave transducer and at least one surface acoustic wave reflector, or at least two transducers is formed on a surface of the substrate opposite the channels at a portion of the substrate that is thinned by the channels, so that the acoustic tracks of the surface acoustic wave device extend along the channels. The response of the surface acoustic wave depends on the response of the sensor material to a sensed fluid supplied to the channels.

15 Claims, 4 Drawing Sheets

U.S. PATENT DOCUMENTS

2005/0148064 A1* 7/2005 Yamakawa et al. ....... 435/287.2
2006/0254356 A1* 11/2006 Liu et al. ...................... 73/592
2007/0000327 A1 1/2007 Sung et al.

OTHER PUBLICATIONS

Ultrasonic and Optical Sensors—Acoustic Plate-Wave Biosensing—White et al—1108 IEEE Engineering In Medicine & Biology Society 11th Annual International Conference CH2770-6/89/0000-1108 C1989 IEEE.

Operation of Acoustic Plate Mode Immunosensors in Complex Biological Media—Morhard et al—Anal. Chem. 1999 71,3150-3156—pp. 3150-3156.

Harmonic Love Wave Devices For Biosensing Applications—McHale et al—Electronic Letters Mar. 15, 2001 vol. 37, No. 6 pp. 340-341.

Layer Guided Shear Horizontal Acoustic Plate Mode Sensors—Martin et al—2002 IEEE International Frequency Control Symposium and PDA Exhibition—pp. 225-233.

Journal Of Applied Physics—Layer Guided Shear Horizontally Polarized Acoustic Plate Modes—Martin et al 2002 American Institute of Physics—May 1, 2002—vol. 91, No. 9 pp. 5735-5744.

Evaluation of Love Waves Chemical Sensors To Detect Organophosphorus Compounds: Comparison To Saw And SII-APM Devices—Chastaing et al—2000 IEEE/EIA International Frequency Control Symposium and Exhibition—pp. 47-51.

SAW Sensors Using Orthogonal Frequency Coding—Hines et al—2004 IEEE International Ultrasonics, Ferroelectrics, and Frequency Control Joint 50th Anniversary Conference—pp. 307-310.

* cited by examiner

ACOUSTIC WAVE ARRAY CHEMICAL AND BIOLOGICAL SENSOR

CROSS REFERENCE TO RELATED APPLICATION

This application claims the benefit U.S. provisional application No. 60/816,464 filed on Jun. 26, 2006, which is incorporated by reference herein

FIELD OF THE INVENTION

The present invention relates generally to a sensor using surface acoustic wave technology and in particular to apparatus, systems, devices, and methods using at least one and preferably multiple acoustic tracks for sensing chemical and biological agents using surface acoustic wave sensors.

BACKGROUND AND BRIEF DESCRIPTION OF THE RELATED ART

Sensors based on surface-launched acoustic wave devices have been developed since the 1980's for application to physical measurements (temperature, pressure, torque, strain, etc.) and to a wide range of chemical and biological detection problems. These widely varying devices have utilized several operating modes and corresponding wave propagation modes, including the traditional Rayleigh wave (or Surface Acoustic Wave—SAW), the surface transverse wave (STW) or the shear horizontal SAW (SH-SAW), the surface skimming bulk wave (SSBW), the SH-SAW or SSBW that has been guided to the surface and into a surface layer of slower acoustic wave velocity, known as the Love wave, the shear-horizontally polarized acoustic plate mode (SH-APM), the flexural plate wave (FPW) or Lamb wave, the layer guided acoustic plate mode (LG-APM), and the thickness shear mode (TSM) bulk wave (as used in the quartz crystal microbalance—QCM). A number of different device types have been recognized using these diverse wave modes, including resonators, delay lines, differential delay lines, and reflective delay lines (tag or ID devices). These devices have been operated within a wide range of wired and wireless interrogation system architectures, which have generally been designed specifically to operate with the selected sensor (s). In most cases, wireless interrogation has been applied to physical sensors, and not to biological or chemical sensors. These system architectures include pulsed radar-like delay measurement systems, Fourier transform measurement systems, and delay line and resonator-based oscillator systems. The system architecture has usually been selected based on specific device characteristics and application requirements, and generally involves absolute or differential measurements of sensor frequency, phase, delay, amplitude, or power spectral density, and changes in these quantities with exposure, to provide the output sensor measurement.

The relative advantages of each wave mode and device type make them suitable for different applications. Rayleigh wave sensors, for instance, involve particle displacements that include a component normal to the substrate surface. When used in a liquid, this component generates a compressional wave in the liquid, causing wave energy to leak into the liquid. This energy leakage results in large attenuation of the Rayleigh wave, often referred to as "damping". This effect makes Rayleigh waves useful only for gas phase sensing, and not applicable to sensing in the liquid phase. This energy leakage occurs whenever the wave motion in the substrate involves a component of displacement normal to the substrate surface, and the speed of the sound wave in the device is greater than the speed of sound in the liquid (or in the layer coating the device). Certain wave modes, such as flexural plate waves (FPWs), do involve a normal component of displacement, but have wave velocities lower than the speed of sound in the liquid. Leakage therefore does not occur, and FPW devices can operate successfully in liquid environments. Other wave modes that do not involve components of displacement normal to the substrate surface are also operable in both gas and liquid phase. These include Love waves, STW or SH-SAW, SH-APM, and LG-APM.

Rayleigh waves coated with polymers have been used extensively for chemical vapor detection. QCM devices have also been applied to characterization of interfacial chemistry in both vapor and liquid environments. In recent years, there has been significant research into the application of STW or SH-SAW, APM, FPW, and Love waves to liquid based biosensing. Michael Thompson and David Stone provide an overview of surface launched acoustic wave sensors in their book, Surface-Launched Acoustic Wave Sensors—Chemical Sensing and Thin-Film Characterization [ISBN 0-471-12794-9, 1997 John Wiley & Sons Inc, NY]. In journal literature, Love waves are often cited as having the highest possible mass sensitivity for example by Electra Gizeli et al., in "A novel Love-plate acoustic sensor utilizing polymer overlayers", *IEEE Transactions on Ultrasonics, Ferroelectrics*, and *Frequency Control*, Vol. 39, No. 5, September 1992, pp. 657-659. STW devices have the practical drawback of difficulty of creating a physical interface between the fluid (liquid or gas) sample chamber and the active device surface. In STW devices, the fluid must be constrained to interact with the surface of the device on which the wave is generated and propagates. This involves making a liquid or gas tight contact on the substrate surface without interfering with the generation and propagation of the acoustic wave. FPW, APM, and LG-APM devices, by comparison, have an advantage in that a gas or liquid sample can interact with the back side of the device, leaving the wave generation process (on the front side of the device) unaffected.

Until recently, most reported FPW devices have been fabricated using silicon substrates with deposited surface layers with desired properties. The silicon substrates are then etched away in the region beneath the sensor active region, leaving a membrane consisting of the surface layer only. These layers may be composed of various films, and the backside of the device may be used to allow exposure of the device to liquid samples, while keeping the electrical connections of the device separated from the sample. Typical films consist of a structural component such as silicon nitride ($Si_3N_4$), combined with a ground electrode layer (often aluminum), followed by a piezoelectric film layer such as zinc oxide (ZnO), and surface fabricated electrodes. In the literature, a good example of this type of device is provided by B. J. Costello et. al., in "Acoustic plate-wave biosensing", *Proceedings of the IEEE Engineering in Medicine and Biology Society* $11^{th}$ *Annual International Conference*, 1989. Composite layer thicknesses typically range from around 3 microns to around 6 microns in thickness, and the resulting devices have operating frequencies in the low MHz range. APM devices, by comparison, have generally been fabricated from plates of piezoelectric materials, often using the thickness of standard wafers. Typical devices may utilize substrates with thickness of 0.5 mm (20 mils). APM devices have been demonstrated on quartz and on high coupling substrates such as lithium niobate. Typical APM devices operate in the low hundred MHz range. In the literature, R. Dahint et. al. discuss APM immunosensors in "Operation of acoustic plate mode immunosensors in complex biological media", *Anal. Chem.* Vol. 71, 1999, pp. 3150-3156. Also in the literature, C. Zimmermann et.al. compare the performance of APM devices with other acoustic sensors in "Evaluation of Love waves chemical sensors to detect organophosphorous compounds: comparison to SAW and SH-APM devices", *Proceedings of the 2000 IEEE International Frequency Control Symposium*, pp. 47-51. In published U.S. Patent Application No. US 2007/0000327 A1, filed Jan. 6, 2006, an acoustic wave sensing device with integrated micro-channels is presented that utilizes flexural plate waves (FPWs) on thinned single crystal piezoelectrics. Both single and double sided processes are discussed for substrate thinning, and protective electrode layers are included to prevent deterioration of the electrodes due to exposure in the sensor. An array of two or more acoustic wave sensing devices are taught, and microfluidic channels connecting the sensing elements are integrated with the FPW devices.

Love wave devices consist of a substrate that is thick relative to an acoustic wavelength (and thus can be viewed as semi-infinite) and a top layer that acts as a guiding layer for the acoustic wave. Generally, the substrate is piezoelectric, such as quartz, and the guiding layer is made of a material with a sound speed lower than the wave speed in the substrate. This structure produces a shear wave with amplitude that decays with depth in the substrate, and with varying amounts of wave energy penetrating the guiding layer (depending on specific device materials and operating parameters). On quartz, amorphous SiO2 and various polymers (PMMA, etc.) are often utilized as the guiding layer. Standard thickness piezoelectric substrates are generally used, with varying thicknesses of guiding layers based on device design. Fundamental and harmonic device operation have been evaluated, resulting in operation frequencies ranging from roughly 100 MHz to over 300 MHz.

Finally, layer-guided SH-APMs (LG-SH-APMs) have been identified as shear horizontally polarized waves that occur in a system that consists of a finite substrate covered by a finite guiding layer of slower shear acoustic speed, and are analogous to either Love waves or to SH-APMs, depending on the precise structure of the device under consideration. It has been suggested that these devices will be capable of higher mass sensitivity than other previously identified device structures. In the literature, Glen McHale et. al. provide a comprehensive discussion of the relationship between Love waves and layer guided SH-APMs in "Layer guided shear horizontal acoustic plate mode sensors", *Proceedings of the 2002 IEEE International Frequency Control Symposium and PDA Exhibition*; and in "Layer guided shear horizontally polarized acoustic plate modes", *Journal of Applied Physics*, Vol. 91, No. 9, pp. 5735-5744. In these publications, the authors clearly explain the close connection between love wave modes, which are shear horizontally polarized surface acoustic waves localized to the surface of a semi-infinite half space by a guiding layer that has a shear acoustic speed less than that of the half space material, and LG-SH-APMs. SH-APMs are resonant shear waves that occur in substrates of finite thickness. These waves do not have wave energy that decays with depth into the substrate as Love waves do, but rather have displacement that is resonant throughout the thickness of the plate, with displacements on both the upper and lower surfaces. Because the wave energy penetrates the entire plate, it is possible (similar to a FPW) to excite an APM with transducers on one side of the substrate and use motion on the other side of the substrate to effect sensing. Placing a layer with slower shear acoustic speed on one side of a substrate capable of supporting SH-APM propagation will result in a LG-SH-APM or a Love wave, depending on the relative thicknesses and shear acoustic speeds of the substrate and film, as well as device operating frequency. These references also make it clear that the high mass sensitivity of Love wave sensors and LG-SH-APM sensors is not due simply to localization of the acoustic wave energy at the surface as widely accepted, rather the high mass sensitivity is primarily due to the combination of high frequency operation and operation in a combined film thickness and frequency regime wherein any change in mass due to surface deposition of an analyte to be measured results in a large change in the phase speed of the wave mode being used. The same can be said for surface changes resulting in changes in physical film properties such as stiffness, elasticity, etc., and for conductivity changes. The large increase in sensitivity possible using LG-SH-APM, combined with the feasibility of exciting these waves using transducers on the substrate face opposite that where sensing takes place makes devices using this construction highly desirable for chemical and biological sensing applications.

Due to the sensitivity of surface-launched acoustic wave sensors to changes in many environmental parameters, it has been customary to utilize some sort of reference device in the sensors or in the sensor systems. This has been accomplished in various ways. For example, differential delay line devices have been used to eliminate variations in electronic signals common to both delay paths, resulting in sensors that are only sensitive to variations in the parameter being sensed. In the literature, the inventor and her research collaborators included differential delay lines in coded SAW sensors for temperature measurement, in "SAW Sensors Using Orthogonal Frequency Coding", *Proceedings of the 2004 IEEE International Ultrasonics, Ferroelectrics, and Frequency Control Symposium*. Similarly, pressure sensors have been developed that utilize multiple transducer and/or reflector structures with wave propagation at different orientations on the substrate to provide information about temperature simultaneously with information about pressure, allowing for the unambiguous determination of both parameters using a single sensor device. U.S. Pat. Nos. 6,571,638 (Hines et. al.), 6,907, 787 B2 (Cook et. al.), and U.S. Patent Application US2005/ 0056098 A1 (Solie) all relate to such sensors.

SAW-based chemical vapor sensor systems have historically utilized multiple polymer-coated SAW sensor devices in an array configuration. Polymers were selected for their chemical orthogonality, or their ability to selectively adsorb or absorb chemical vapors of interest. Patterns of vapor responses developed on the multi sensor arrays could then be characterized using pattern recognition techniques. Reference sensors that were hermetically sealed or otherwise protected from exposure to the vapors under test were generally included in the arrays in order to allow for accurate determination of the array response. These arrays were often temperature controlled, either through bulk temperature control of the sensor devices (using under package heating and cooling) or through on-chip heaters incorporated in the sensor devices. These temperature control elements (including on-chip heaters) could be used to thermally ramp sensors and observe the temperature (and thus time) dependent desorption of adsorbed of vapors, providing an additional metric useful for pattern recognition. Prior acoustic wave biosensor devices have generally been used individually or in pairs, where one device serves as a reference device for the pair. In all cases known to the inventor where arrays of sensors have been used in biological and/or chemical sensing (prior to published U.S. Patent Application No. US 2007/0000327 A1, filed Jan. 6, 2006) the array has been composed of multiple individual distinct sensor devices along with measurement electronics. Depending on the system configuration, the measurement electronics may be common ("shared" and used sequentially by all sensors in the array), or multi-channel electronics may be used, allowing the simultaneous (or near-simultaneous) measurement of all array elements. U.S. Patent Application No. US 2007/0000327 A1 introduces an acoustic wave array sensing device with integrated micro-channels that utilizes flexural plate waves (FPWs) on thinned single crystal piezoelectrics. Integration of microfluidic channels connecting the sensing elements and utilization of a FPW acoustic mode are advantageous characteristics of that approach.

Prior SAW based RF ID tags and physical sensors have utilized various coding techniques to allow identification of individual sensors within multisensor networks. Such sensors have also been accessed primarily via wireless radio frequency (RF) communication techniques. To date, the ability to incorporate unique sensor identification and the potential wireless operation aspect of these sensors has not been exploited for chemical and biological sensing applications in vapors and liquids.

SUMMARY OF THE INVENTION

The present invention relates to devices and methods for providing acoustic wave array sensors incorporating coding for use in the simultaneous measurement of one or more parameters. Specifically, the invention relates to a layer guided shear horizontal acoustic plate mode array device that utilizes thinned single crystal piezoelectric substrates as sensing regions and incorporates multiple microfluidic channels integral to the substrate, with individual coding and different functionalization of each channel possible to provide simultaneous multiple channel sensor identification and measurement information.

Unlike prior individual and array acoustic wave sensors, the sensor array devices according to one embodiment of the invention require no protective coating over electrode regions, and can be manufactured and assembled using standard flip chip assembly and standard ceramic surface mount packaging techniques. Also unlike prior array acoustic wave sensors, the devices according to an embodiment of the invention can use utilize frequency diversity among channels or coding of individual channels to effect identification of individual sensor channel response. Additionally, sensor array devices according to an embodiment of the invention can utilize proper functionalization of the multiple channels together with channel identification to produce simultaneous measurements of multiple parameters. This can be useful when measuring multiple physical parameters, or when analyzing fluids (liquids and vapors) to determine the presence, absence, or concentration of a specific chemical or biological component. Also unlike prior acoustic wave array devices, the LG-SH-APM array devices according to an embodiment of the invention utilize the highly sensitive layer guided shear horizontal acoustic plate mode wave propagation mode, which when properly designed can produce sensor sensitivities more than an order of magnitude greater than those of conventional SH-APM devices and other acoustic wave sensors.

DETAILED DESCRIPTION OF THE PREFERRED EMBODIMENTS

The acoustic wave array sensors of embodiments of the current invention utilize four fundamentally different elements to realize advantages over prior art acoustic wave sensor array techniques. First, sensor embodiments utilize layer guided shear horizontal acoustic plate mode (LG-SH-APM) waves and associated Love waves propagating in thin-layer single crystal piezoelectric substrates coated with guiding layers to achieve enhanced sensor sensitivity. Multiple integrated microfluidic channels are utilized for ease of manufacturing and sample handling. Second, sensor embodiments utilize frequency diversity among channels or coding of individual channels to effect identification of individual sensor channel responses. Third, functionalization of separate channels is used together with channel identification, to produce simultaneous measurements of multiple parameters. Fourth, sensor embodiments utilize guiding layers placed on the substrate surface opposite the surface where the electrodes are located, and sensing occurs on the side of the sensor array containing these guiding layers. Hence, no protective layers are needed in the electrode regions of array sensors according to some embodiments of the present invention. The implementation and benefits of each of these elements is described briefly below.

As mentioned above, sensor embodiments utilize layer guided shear horizontal acoustic plate mode (LG-SH-APM) waves and associated Love waves propagating in thin-layer single crystal piezoelectric substrates with appropriate guiding layers. The thin-layer regions in which the LG-SH-APM waves propagate are created by known micromachining processes. Micromachining in this context means structures on the micro or nano scale formed using any combination of fabrication processes including wet chemical etching, dry etching, grinding, physical ablation, and other processes utilized within the MEM (microelectromechanical) device industry. A single sided process is preferred as it leaves the untreated side of the wafer available for standard photolithographic production of the transducer and reflector structures used in generation and processing of the acoustic wave. Use of thinned single crystal piezoelectrics (such as quartz, lithium niobate, lithium tantalate, crystals in the langasite family, and other known single crystal piezoelectrics) produces substrates with higher electromechanical coupling coefficient than the bulk materials and better temperature stability (for certain substrates) and film quality than thin piezoelectric films grown of similar materials on other substrates and subsequently "released" by etching away of the substrate.

The LG-SH-APM waves utilized in embodiments of the present invention occur in piezoelectrics of finite thickness when a guiding layer comprising a material with a slower shear acoustic speed is formed on one surface of the piezoelectric. As Glen McHale et. al. show in FIG. 5 of "Layer guided shear horizontal acoustic plate mode sensors", *Proceedings of the* 2002 *IEEE International Frequency Control Symposium and PDA Exhibition*, the substrate displacement of the first SH-APM mode in a finite piezoelectric without any guiding layer is distributed antisymetrically through the thickness of the plate, with the top and bottom surfaces moving in such a way that a resonance condition exists with the surfaces one half wavelength out of phase. As a layer of non-zero thickness is added to one side of the SH-APM substrate, the substrate displacement very quickly becomes nearly constant within the substrate, and the displacement becomes a half wavelength within the layer. The displacement therefore changes very rapidly within what is normally a very thin guiding layer. This produces a structure in which a small change in guiding layer thickness can cause a rapid change in phase speed of the wave in the layer. The high sensitivity achievable with these sensors is due to this rapid change in phase speed with layer thickness or mass loading.

In an operating sensor, binding of the analyte of interest will have the same effect as a slight increase in guiding layer thickness. Since the device will be designed to operate in the region with the steepest slope of phase speed vs. normalized guiding layer thickness, even slight variations in film mass will result in large changes in sensor phase velocity. While phase velocity is not the same as group velocity and hence is not directly reflected in device delay, these changes will be translated deterministically into variations in acoustic wave frequency, delay, insertion loss, or other parameters that can be measured. It should be noted that deposition of increased mass with acoustic shear speed lower than the substrate acoustic shear speed can result in conversion of the LG-SH-APM into higher order Love waves. These two wave modes, while different, are in fact modes that are solutions to the wave equation with boundary conditions that produce either real or complex wave vectors. SH-APM modes correspond to the conditions under which the substrate wave vector is purely imaginary, while Love waves correspond to conditions that result in a purely real wave vector in the substrate. Addition of guiding layers with lower shear acoustic speed and different wave vectors result in families of wave modes that can include higher order Love waves and LG-SH-APMs, depending on the details of the device configuration. While both LG-SH-APM and Love waves can be used in sensing, carefully device design and guiding layer optimization will be required to obtain sensors that operate in the high sensitivity region for specific fluid environments. In certain cases, use of an extremely thin guiding layer, such as a self-assembled monolayer or a nanocluster layer may be sufficient to produce layer guiding of the SH-APM. In other cases, the loading introduced by the fluid being analyzed may be sufficient to produce the desired effect. In any event, device design and optimization will be strongly dependent on the specific intended application environment.

The substrate to be used in each embodiment of the present invention will depend on the requirements for bandwidth and temperature stability. Multiple integrated microfluidic channels are utilized in the current device. Unlike prior acoustic wave array devices incorporating microfluidic channels, these channels are preferably physically separate from one another, with no cross-connections that would allow fluid samples to flow between channels. The channels may be fed from a common input plenum or discrete plenums, and waste from each channel may flow into an individual outlet or into a common outlet plenum. This enhances ease of manufacturing of arrays with different functionalization on each channel as described below, and also enhances ease of fluid sample handling in applications. Specific covers incorporating fluid handling can be used to simultaneously or individually provide specific coatings to each channel, or lithographic techniques can be used to selectively deposit coatings. Once the array has been coated appropriately, a different cover can be permanently attached to provide fluid handling in the final array sensor chip. The entire process can be done cost effectively, producing completely disposable, single-use sensors.

Sensor embodiments of the present invention utilize frequency diversity among channels or coding of individual channels to effect identification of individual sensor channel responses. Electrode and busbar structures are formed on the non-sensing side of the array in order to produce transducers that can launch acoustic waves in response to an incident signal. This signal or set of signals can be provided through wires, or through an RF (radio frequency) signal incident on an antenna or set of antennas connected to transducers on the surface. In the preferred embodiment, at least one transducer is needed in each channel, and can take the form of any of a multitude of transducer structures known in the art. Additional transducers, reflectors, and other SAW elements known in the art can be utilized to effect the desired signal processing functions in each channel. Multi-strip couplers can also be utilized to transfer acoustic energy from channel to channel. While the channels shown in the preferred embodiment are parallel, this is not a requirement, and certain sensors may take advantage of having channels at different angles on the substrate, utilizing waves propagating in different crystallographic directions. Any known SAW elements, including but not limited to dispersive delay lines, inclined transducers, tapered transducers, reflective array compressor structures, and correlators may prove advantageous for certain purposes, and their use in a LG-SH-APM array sensor device is considered within the scope of the present invention.

The simplest form of frequency diversity is provided by having single frequency resonator or delay line (single sided or differential) structures operable in each channel, with the center frequencies offset enough to provide differentiation over the entire operating range of sensed and environmental parameters. In this case, the overall signal can be divided into frequency ranges corresponding to each channel, and the sensor response can be measured by the response (amplitude, delay, phase, and/or frequency) of the signal in that frequency band. Another method for providing identification of individual channel responses is time division multiplexing—i.e. each channel can be designed with a specific differential delay (to eliminate common delay issues) that is distinct from other channels. The delay range into which the response falls would then identify the channel, while the measurement of the differential delay would produce the sensed parameter value. A third possibility for channel identification is inclusion of unique codes in each channel. This can be done using any of a wide range of known coding techniques, including but not limited to pseudo-noise (PN), magnitude shift keying (MSK), phase shift keying (PSK), on-off keying (OOK), orthogonal frequency coding (OFC), and a newly invented SAW coding technique called discrete frequency coding (DFC). DFC, which was conceived by the inventor and her colleague Dr. Leland Solie coincidentally with the present invention, is a SAW coding technique for transmission of sensor identification and information using tapered SAW elements and multiple acoustic tracks. The discrete frequency response method and apparatus is the subject of copending application Ser. No. 60/816,578, filed on Jun. 26, 2006, and a non-provisional application Ser. No. 11/768,428, filed on Jun. 26, 2007, claiming the benefit thereof. The discrete frequency responses of the elements in the acoustic channels comprising the DFC code provide enhanced chip orthogonality relative to known techniques such as OFC, providing improved codesets with lower inter-chip interference levels. DFC can be used in the present device with a different code within each acoustic track (corresponding to each Microfluidic channel), or across the array. It will be understood by one skilled in the art that these coding techniques can be combined to provide enhanced codesets if increased number of unique codes are needed.

Another significant advantage of embodiments of the present invention relative to prior art is the functionalization of separate channels. Taken together with channel identification previously discussed, this enables simultaneous measurements of multiple parameters. This can be useful when measuring multiple physical parameters including temperature, pressure, and strain. It can also be useful for analyzing fluids (liquids and vapors) to determine the presence, absence, or concentration of a specific chemical or biological component. Functionalization can take many forms, but in the preferred embodiments of the present invention it generally refers to the chemical modification of the surface through deposition of a specific layer. This can be a layer covalently bound to the surface, or a layer physically in contact with the surface. It can be a layer as thin as a self assembled monolayer or a nanocluster or nanomaterial layer, or it can be as thick as a polymer layer such as PMMA or photoresist. In order to be a suitable guiding layer for the SH-APM waves, the functionalization must produce a layer with a slower shear acoustic wave speed than that of the substrate. The requisite slowing of wave speed can be accomplished due to physical properties of the film, including elasticity, stiffness, dielectric characteristics, viscosity, conductivity, or any other property capable of influencing shear acoustic wave speed in the layer. For certain applications, mass loading of a vapor or liquid may be sufficient to produce this effect.

For chemical sensing, the preferred embodiment of the present invention uses different coatings in each channel, with coatings selected for their degree of chemical orthogonality (i.e. the ability of the coatings to respond to certain chemical or classes of chemicals and not others). The relative responses of the channels generated, taken together with pattern recognition can be used to identify and quantify certain components of the mixture. This approach is quite similar to the approach previously used with arrays of individual polymer coated SAW sensors for detection and quantification of a wide range of analytes. Chemical agents, volatile organic chemicals, toxic industrial chemicals, and others have been detected using such polymer coatings. Metal oxide coatings have been used to detect other chemicals in the vapor phase, as have nanocluster metals. In the liquid phase, acoustic wave devices have been used with various coatings and metal compositions to detect heavy metals and a range of other pollutants and chemicals. Any of the coatings known in the art as compatible with bulk or surface acoustic wave devices for detection of species can potentially be used in the current invention.

For biological sensing, highly specific coatings for certain biological moieties of interest (bacteria, cells, proteins, DNA, RNS, etc.) can be used. Each channel can be coated with a different biologically specific coating. A single sample of a fluid containing unknown bacterial components can then be passed through an array for determination of the presence of any of the specific biological moieties included in the array. This is highly useful for point of care clinical diagnosis and can be used, by way of example, to produce chips functionalized to look for families of related infections. An "STD chip" could be functionalized to look for Chlamydia, Gonorrhea, Syphilis, etc. In this example, the biological species being detected are the different bacteria strains responsible for these infections. A single sample from a patient could be processed through this array sensor chip, and the resulting measurements would tell the physician in near real-time that the patient has or does not have an infection caused by each type of bacteria. The extremely high mass sensitivity of the acoustic wave device allows such a determination to be made without any culturing, growth of the sample, or DNA/RNA amplification technology. This results in a substantially less expensive, more rapid diagnostic tool. The array sensor embodiments of the present invention utilize the spatial diversity provided by multiple microfluidic channels, combined with different coatings and frequency diversity to ID multiple analytes from a single sample and measurement process.

Finally, sensor embodiments of the current invention utilize guiding layers placed on the substrate surface opposite the surface where the electrodes are located, and sensing occurs on the side of the sensor array containing these guiding layers. Hence, sensor arrays according to the present invention can be packaged using standard SAW device flip chip assembly procedures and standard ceramic surface mount packages. This embodiment of the current invention overcomes the limitations of the prior art, wherein protective layers were required over the transducer regions. No such layers are needed in array sensors according to the present invention. The integrated microfluidic channels of the present invention, taken together with the ease of production and packaging considerations, produce an array sensor that can be manufactured in a cost effective fashion, making truly disposable array sensors feasible. This is a significant advantage, particularly for the point-of-care clinical diagnostic applications such as the STD chip mentioned previously.

Knowing the advantages provided by the use of the elements of this invention, numerous embodiments of the present invention are possible. It will be evident to one skilled in the art that the principles of the current invention provides the designer with a considerable degree of flexibility. For example, channels may be used at any desired angles on substrates, and the designer can even combine different wave modes and device operating principles and frequencies within one array sensor chip if it provides added information. Device configurations that can be used in each channel include resonant SAW structures, delay line and differential delay line structures, coded and non-coded structures, tag structures, one-port structures, two-port structures appropriate for impedance loading of one port, fundamental operation, harmonic operation, etc. All of these embodiments and others that would be evident to one skilled in the art are within the scope of the present invention.

BRIEF DESCRIPTION OF THE FIGURES

Other objects and advantages of the invention will become apparent from a study of the following specification when viewed in the light of the accompanying drawing, in which.

DETAILED DESCRIPTION OF THE DRAWINGS

Figure 1A:
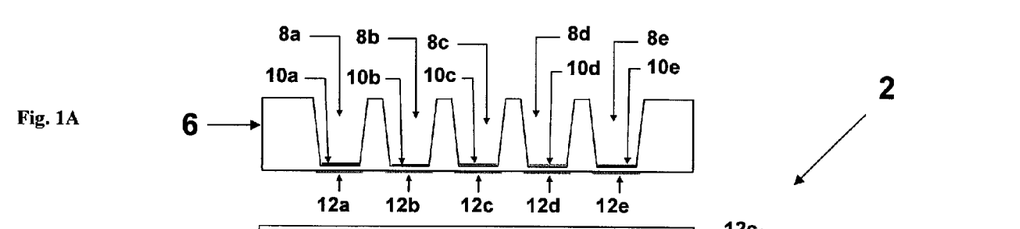
FIGS. 1A and 1B are an end view and a top plan view of a sensing side (hereinafter referred to as "top") of a frequency diverse and time diverse differential delay line array sensor incorporating microfluidic channels and sensing guiding layers in each channel according to the principles of the invention.
Figure 1B:
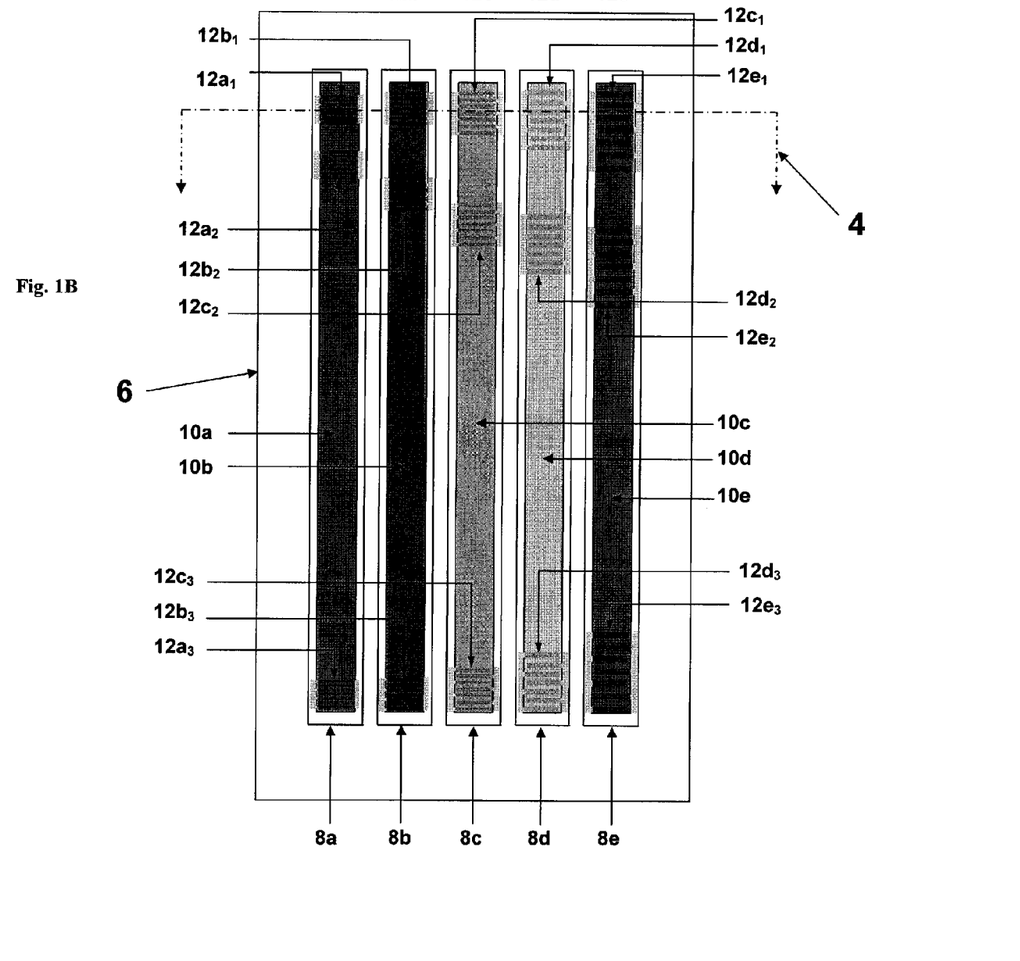

Referring first to FIGS. 1A and 1B, there is shown an array sensor 2 according to an embodiment of the present invention. The lower diagram in FIG. 1B shows a top view of the device, and the upper diagram FIG. 1A shows a cross sectional view taken through the device at the position indicated by the dashed arrow 4. The device includes a piezoelectric substrate 6 into which are machined multiple microfluidic channels 8

(shown as channels 8a, 8b, 8c, 8d and 8e). These channels serve as conduits for fluids to be measured, and when capped as shown in later figures, enable directed fluid sample inflow and outflow. This example illustrates an array with five channels, each coated with a different layer. These layers 10 (shown as layers 10a, 10b, 10c, 10d and 10e) serve to both guide the SH-APM waves into LG-AH-APM waves, and to interact with the environment to detect analytes of interest. The layers can vary in thickness and composition, and may include chemical functional groups or biological moieties that bind specifically to known analytes. Transducers 12 (shown as transducers 12a, 12b, 12c, 12d and 12e) are located on the bottom of the array substrate.

In the example of FIGS. 1A and 1B, each channel has three transducers, for example in channel 8a, the end transducers are $12a_1$ and $12a_3$ while the transducer that lies therebetween is $12a_2$. A similar designation is provided for the transducers of each channel. The transducer $12x_2$ that lies between the end transducers operates to transduce an incoming electrical signal into an acoustic wave. This wave propagates in both directions along the thinned piezoelectric channel region, interacting with first with the closer of the two outer transducers $12x_1$ and later with the transducer $12x_3$ that is farther away. These transducers $12x_1$ and $12x_3$ convert the acoustic wave signal back into electrical signals, which are communicated back to the interrogator for signal processing and interpretation. This configuration is an array of two-port differential delay lines.

It should be noted that in the example of FIGS. 1A and 1B, each channel has transducers with a specific center frequency, determined by the electrode periodicity. This provides frequency diversity between the channels. In addition, each channel has the transducers located at different separation distances, so that the differential delay (i.e. the difference in the acoustic wave propagation delay to the two outer transducers) differs for each channel. This provides another mechanism for identifying which channel returning signals originate from. It will be evident to one skilled in the art that the interpretation of signals produced by this structure can be accomplished in a number of ways. In addition, it will be clear that in some applications it may be advantageous to provide a "wall" underneath the center transducer. This can be accomplished during etching of the channels by using a different etching geometry. Such a construct effectively isolates the two sides of each channel from one another. This can provide a useful reference path (generally the shorter delay), which can be coated with the same guiding and sensing layer as the longer sensing path, but which is not exposed to analyte-containing fluid samples The reference may be exposed to a reference fluid not containing the analyte of interest if necessary to provide a good reference. Such a reference can be useful in compensating for common effects in the sensors, such as temperature variation. There may also be instances where the same coating will be used in more than one channel, and device frequency (fundamental or harmonic operation), delay, or signal amplitude will be used as a metric.

It will also be evident to one skilled in the art that the transducer structures shown in FIG. 1 are for illustrative purposes only, and represent only one of a wide range of possible device topographies that are well known in the art and would be useful when incorporated into the present array sensor. Such useful device topographies include resonators, reflective delay lines and reflective differential delay lines, correlators, dispersive devices, coded devices such as PN, OFC, and DFC, and devices incorporating inclined transducers, or tapered, stepped tapered, and slanted transducers. Interrogation techniques appropriate to each approach are known in the art.

Figure 2A:
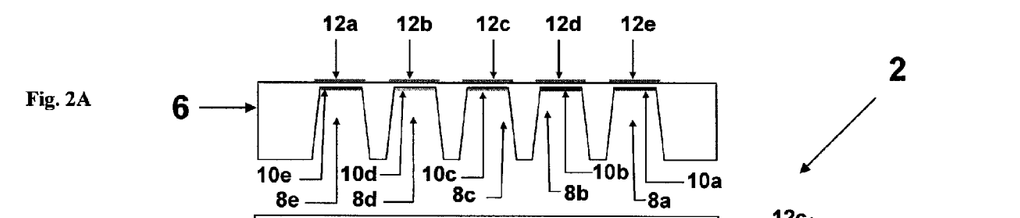
FIGS. 2A and 2B are an end view and a bottom plan view of a side (the side opposite the sensing side) of the frequency and time diverse differential delay line array sensor of FIGS. 1A and 1B.
Figure 2B:
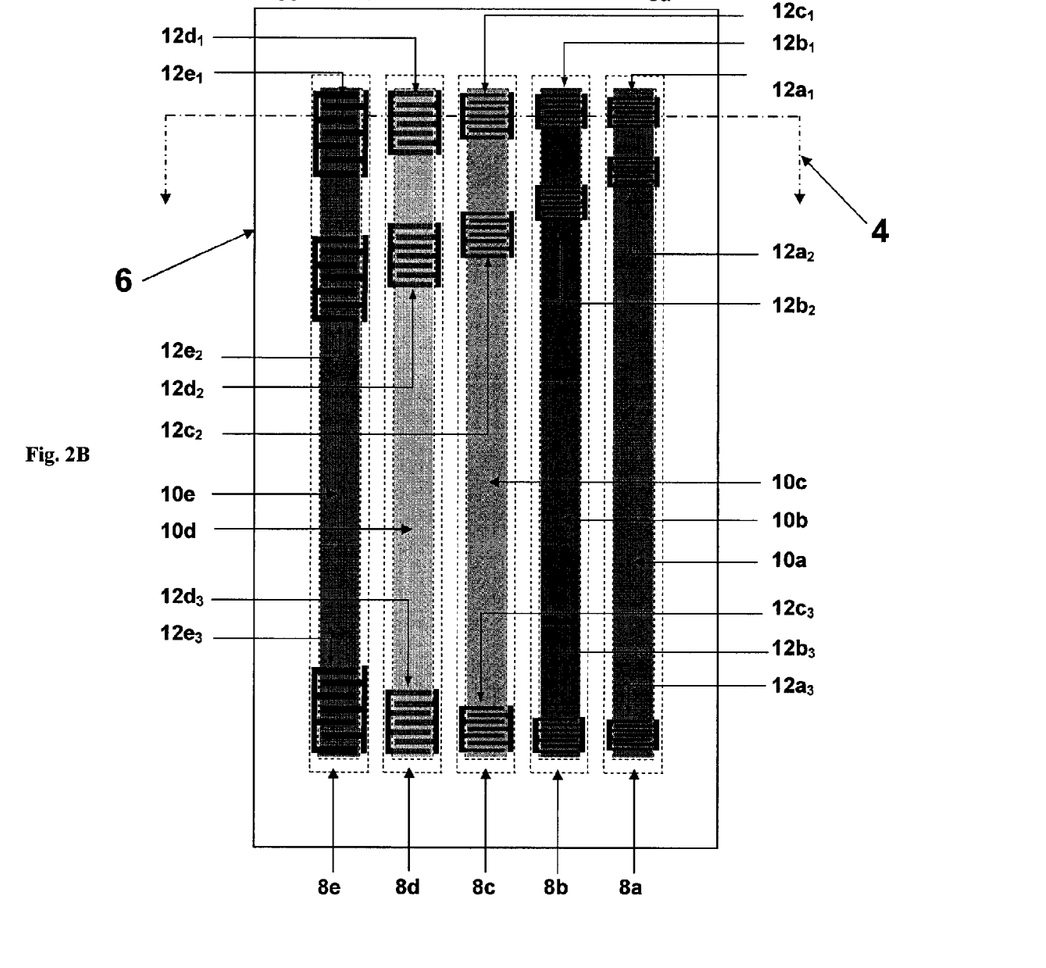

In FIGS. 2A and 2B, there are shown additional views of an array sensor 2 according to the present invention. The lower diagram in FIG. 2B shows a bottom view of the device, and the upper diagram in FIG. 2A shows a cross sectional view taken through the device at the position indicated by the dashed arrow 4. As in FIG. 1, the device includes a piezoelectric substrate 6 into which are machined multiple microfluidic channels 8 (shown as channels 8a, 8b, 8c, 8d and 8e) (here seen through the substrate wafer), with each coated with a different layer. These layers 10 (shown as layers 10a, 10b, 10c 10d and 10e) serve to both guide the SH-APM waves into LG-AH-APM waves, and to interact with the environment to detect analytes of interest. The transducers 12 (shown as transducers 12a, 12b, 12c, 12d and 12e) are located on the surface of the array substrate opposite the channels, which is up in the view of FIG. 2A. As in FIGS. 1A and 1B, each channel has three transducers 12 arranged in a two-port differential delay line configuration. It can be seen again in FIG. 2 that each channel has transducers with a specific center frequency, located to provide different differential delays.

Figure 3:
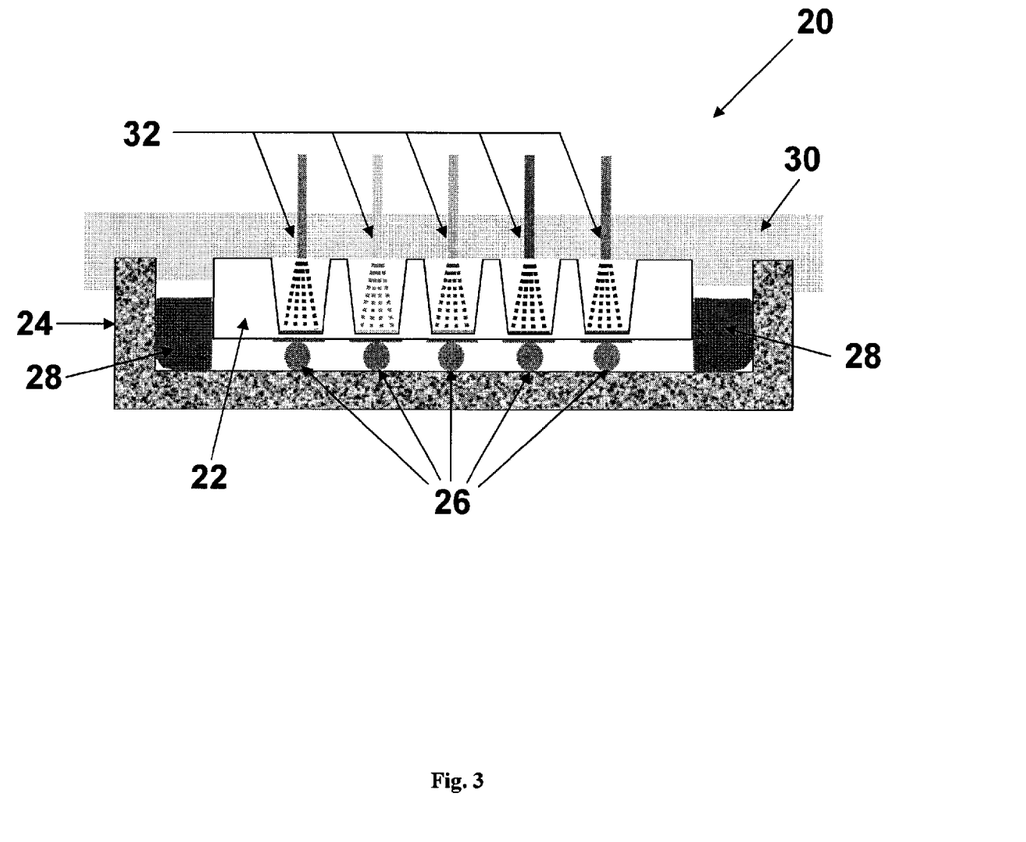
FIG. 3 is a cross sectional view of an array sensor incorporating microfluidic channels and a fabrication cap designed to enable simultaneous functionalization of each channel with different sensing and guiding layers according to the invention.

Referring next to FIG. 3, there is shown therein a cross sectional view of an array sensor 20 incorporating microfluidic channels and a fabrication cap designed to enable simultaneous fictionalization of each channel with different sensing and guiding layers according to the invention. The sensing and guiding layer for each channel may be of one material, or the guiding layer may be of one material while the sensing layer is of another material. The sensor array 20 is assembled top side up (microfluidic channels up) into a standard ceramic surface mount package 24. Standard flip chip mounting techniques such as gold ball bump bonds 26 can be used to attach the die to the package mechanically, and to make electrical connections to the transducer structures used to launch and receive the acoustic waves. It will be understood by those skilled in the art that additional bond pads and busbars will be required on the surface of the die in order to connect electrical pads in the SMP package to the transducer elements. Once the die has been mounted, a sealing compound 28 is placed around the perimeter of the die, effectively sealing the cavity under the die and preventing infiltration of fluids capable of damaging the electrode structures. This alleviates the need for a protective coating over the electrode regions, as reported in the prior art. The sealing material of choice will depend on a number of issues, including the composition of the electrodes, thermal expansion characteristics of the array sensor die and package, and thermal and chemical environment to which the finished sensor is likely to be exposed. For some applications, a simple room temperature curing conformal material such as RTV may be used. Other materials requiring UV curing, or any of an assortment of epoxy materials may also be used under appropriate circumstances. Outgassing of such materials during cure will be of concern, and materials with low outgassing and/or solvents compatible with device electrode metallization should be used.

It is significant to note, however, that for many intended uses of the current invention, these sensor arrays will be single-use, disposable sensors. Thus a high degree of hermeticity is generally not required. Rather, the sealing material must be impenetrable enough to prevent infiltration of undesirable materials into the cavity between the die and package both during the guiding/sensing layer fabrication process and during sensor use (which is generally rather brief). If a particular application requires a more hermetic seal, any of a wide range of known package sealing techniques, including but not limited to spin on glasses, glass frit technology, solder sealing, and others may be utilized. A fairly conformal cap 30 is placed in firm contact with the package and the array sensor die. This cap can be made of any material, but generally a somewhat compliant, dimensionally stable, chemically inert material such as Teflon® is preferred. The cap can be dimensioned so that it snaps onto the base, and also makes firm contact with the die walls between channels. If desired, additional sealing material can be used on the bottom of the cap to provide a better seal between the cover and the channel walls. In the cap, there have been produced feed-through holes 32, into which tubing can be inserted for introduction of appropriate coating materials. Similar outlet holes and tubing can be provided at the other end of each channel to allow fluid flow through the channel. Such a cap configuration can be used during device production to simultaneously or sequentially introduce coating materials into the channels. This approach allows easy coating of different channels with different coatings. It will be understood to one skilled in the art that other cap configurations would be preferred for different coating types. For example, a physical masking approach (using, for example, a machined silicon wafer or metal mask) can be used to protect all but the selected channel(s) when metal and metal oxide films are to be deposited via sputtering or evaporation procedures. Once channel coating is completed, this fabrication cover can be removed from the array sensor package, and a cover appropriate for the end product can be permanently installed.

Figure 4:
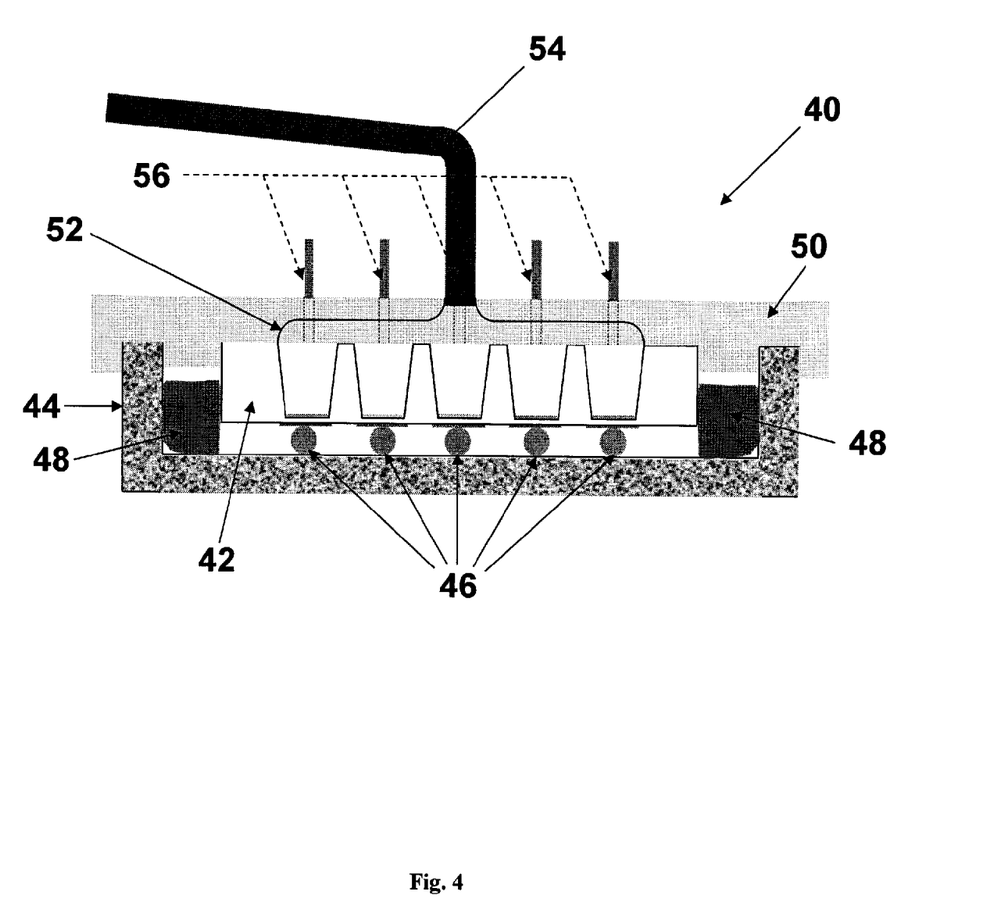
FIG. 4 is a cross sectional view of a packaged array sensor incorporating microfluidic channels with different sensing and guiding layers and a permanently affixed cover designed to direct fluid into and through the array sensor channels according to the invention.

FIG. 4 shows a cross sectional view of a packaged array sensor 40 incorporating microfluidic channels with different sensing and guiding layers according to the invention, that also comprises a permanently affixed cover designed to direct fluid into and through the array sensor channels. As in FIG. 3, the array sensor 42 is mounted in a surface mount package 44 using standard flip chip bump bonds 46, and sealing material 48 is applied to seal the cavity under the die and preventing infiltration of fluids capable of damaging the electrode structures during use. After the channels have been coated with guiding and sensing layers (which may comprise single or composite layered structures), a cover 50 is permanently affixed to the sensor array package. The cover 50 should be structured to allow adequate flow of sample fluids into and out of the sensor array channels. This can be accomplished using individual inlet and outlet tubing connections as shown in FIG. 3.

An alternate preferred embodiment shown in FIG. 4 has an inlet plenum 52 formed into the cover, allowing a fluid sample to flow in through one common inlet tube 54 and be evenly distributed to all channels of the array sensor. Adequate modeling of the fluid flow in the small cavities of such a package will be necessary in order to ensure even sample distribution and to avoid problems with dead space and turbulence. FIG. 4 shows independent outlets 56 from the individual channels, but an alternate embodiment could utilize a common outlet plenum similar in nature to 52 for disposition of sample fluids after they pas through the array. The cover 50 may be made of a wide range of materials suitable to both the sealing requirements and manufacturing processes. For example, a metal cover can be milled or formed, and may be sealed to the package 44 using any of a range of standard sealing techniques. Solder preforms are commonly used on metal covers for SMP packages. In this case, a thin controlled layer of solder is placed in specific locations on the back of the cover, where the cover will come in contact with the rim of the package. The cover also generally has some indentations that ensure proper alignment during use. Passing the device through a solder reflow oven allows the solder to melt and seal the device. In the present invention, solder preforms could be used to provide a seal to the back of the die around each channel as well. Of course, the heating process involved in the use of solder reflow techniques may preclude the use of this approach for array sensors utilizing coatings that could be changed or damaged by high temperatures. In such cases, any alternate cover material can be used. Teflon, ceramics, and other materials can be used, and can be combined with adhesive and epoxy sealing techniques as appropriate.

Other embodiments that utilize LG-SH-APM wave modes on thinned single crystal piezoelectric substrates along with multiple microfluidic channels coated with layers for guiding the wave and sensing analytes, and including frequency diversity, time diversity, and/or coding of the channel responses for identification are within the scope of this invention. Interrogation and signal processing techniques appropriate to the acoustic wave device structures selected can be used, and may include pulsed radar architectures, Fourier transform measurement systems, delay line and resonator-based oscillator systems, and power spectral density time integrating correlators approaches. It will be apparent to those of ordinary skill in the art that the invention can be implemented as a single or multiple sensor array system, with wired or wireless communication between the transceiver and the sensor(s). Multiple transceivers and/or signal repeaters may be utilized for large multi-sensor systems. Practical systems utilizing the invention may include a computer, microprocessor, or other calculating devices, and the necessary software for performing necessary calculations based on measured array sensor responses. Such systems may include the ability to uniquely identify individual sensor channels and the data therefrom. Additional aspects of a practical system utilizing the invention include the ability to store data and calculation results, and devices for transmitting the data and/or results to entities interested in the results. Such transmission of information may include but is not limited to communicating to external computers, web sites, cell phones, and other devices.

Use of arrays of discrete acoustic wave sensors for simultaneous determination of multiple measurands is widely known in the art. Since the 1980's, researchers have utilized arrays of multiple SAW devices coated with different chemically selective polymers to detect, identify, and quantify chemical vapors, both alone and in mixtures. Polymers such as poly(ethylenimine) (PEI), fluoropolyl (FPOL), nation (NAF), poly(epichlorhydrin) (PECH) and poly(ethylene maleate) (PEM) are recognized as useful for such applications. In a discrete sensor array, a group of polymers will be utilized that provide somewhat orthogonal responses to chemicals of different classes, and each device will be coated with one of the selected group of polymers. When the group of sensors is exposed to a vapor containing either a single component or a mixtures of chemicals, each polymer coated device responds with a different reaction to the vapor sample. Certain polymers will react strongly to aromatic compounds such as benzene and toluene, other polymers react more strongly to chlorinated compounds such as trichloroethylene and carbon tetrachloride, and yet other polymers will respond strongly to aliphatic compounds such as hexane. Using each polymer as a "dimension", a multi-dimensional pattern can be formed from the overall array response. Pattern recognition techniques such as principle components analysis (PCA), K-Nearest Neighbors, and similar techniques can then be used to analyze the pattern generated by the sensor array. Such sensor arrays and analysis techniques have been successfully utilized to detect, identify, and even quantify chemical vapors ranging from chemical warfare agents to toxic industrial chemicals. The polymers used in such sensors can be applied to the present devices as layers that provide both guiding of the acoustic wave and selectivity for a class of chemicals. Specific coating characteristics, such as thickness, will vary from channel to channel in order to optimize layer guiding of the wave.

Specialized polymers such as phthalocyanines (with and without metals), silane based compounds, and others are known to form self assembled monolayers on substrates including piezoelectrics. Depending on the thickness of the thinned piezoelectric region, the properties of these films, and the operating frequency of the device, such films may be suitable to provide layer guided waves. Such films can generally be deposited in a controlled manner in single or multiple molecular layers to achieve a desired coating thickness. For some device configurations, and some liquid environments, the presence of a liquid itself may provide the boundary conditions required to provide layer guiding of the wave. This is most likely to occur in liquids of high viscosity.

In addition to polymers, various other coatings can be used to provide target selectivity and guiding of the acoustic wave in the present devices. Metal oxides have been widely used on discrete acoustic wave sensor devices to detect small vapor molecules, such as carbon dioxide, nitrous oxide, and sulfur dioxide. Metal layers, both pure and alloyed, have been used in thick film, thin film, and nanostructure form to detect other chemicals. For example, palladium is widely recognized as a metal coating useful for detection of hydrogen gas. When used as a film on an acoustic wave device, the palladium undergoes a change in film conductivity due to exposure to hydrogen gas. This change in conductivity causes a change in acoustic wave propagation velocity, with the magnitude and speed of the change depending on the specific film structure. Such metals and metal oxides can also be used in the present array devices to accomplish guiding o the wave and specific analyte detection.

Another application of discrete acoustic wave sensors that is extensible to the present devices is biological sensing. Polymeric layers such as polymethylethacrylate (PMMA) have been widely used on acoustic wave devices to produce love waves. Metals that are relatively chemically inert such as gold have also been used in biological sensing applications. In either case, these coatings are generally functionalized with biologically specific moieties that can make the sensor detect the target of interest. For example, the specificity of antibody-antigen reactions makes this reaction an ideal way to identify bacteria. The surface biochemistry of bacteria of interest must first be known. Then, an antibody that specifically binds to an antigen commonly occurring on the outer surface of the bacteria can be tethered to the coating on the acoustic wave device. Such tethering can be accomplished through any of a number of well known approaches, such as exploiting a thiol group to link the antibody to a gold layer. Provided the interaction is suitable specific, fluids containing the target bacteria will bind to the surface of the device, causing relatively large mass loading changes, and corresponding acoustic wave device performance changes.

It is evident that all of these materials and approaches may be applied in the present devices to implement array sensors capable of performing biological sensing. A single sample can be analyzed for the presence or absence of multiple biological targets, in a single pass through the sensor array. Such a device could be useful for diagnosis of infections out of a group of possible infections that afflict the same region of the body (respiratory diseases, sexually transmitted diseases, etc.). Or, redundancy can be incorporated into the array to provide greater assurance of the response to a single target, as might be desirable for biological agent detection.

Finally, it should be recognized that in addition to being used as an array sensor to detect targets in a sample (or the environment), the present device can be used to detect properties of the layers coating the microfluidic channels. SAW sensors were first identified for use in detecting changes in polymeric layers deposited on their surfaces. The present device would make a sensitive tool for evaluating one or more layers of any suitable material for phase changes, glass transitions, and changes in stress, strain, elasticity, viscosity, dielectric constant, and similar properties. All such applications of the present device are understood to have benefits over the related prior art approaches using arrays of discrete sensor devices.

While it would be impossible to generate a comprehensive list of all potential analytes of interest, it is clear that this group may include chemicals such as volatile organic chemicals (VOCs), toxic industrial chemicals (TICs), heavy metals, and chemical warfare agents, and biological moieties such as bacteria, proteins, antibodies, antigens, DNA, RNA (or fragments thereof), vesicles, lipids, cells, and a range of other possible moieties. The fluid in which the analytes of interest are present may be vapor or liquid phase. These sensor array devices are also capable of measuring physical parameters of interest such as temperature and pressure.

Thus, there is shown and described an acoustic wave sensor array device for the detection, identification, and quantification of chemicals and biological elements dispersed in fluids. The sensor array device is capable of the simultaneous characterization of a fluid for multiple analytes of interest. A substrate has a plurality of channels formed therein and a sensor material layer applied in a bottom of the channels. The sensor material layer has a shear acoustic wave speed lower than a shear acoustic wave speed in said substrate. The channels may have the same material in each channel or different materials in at least two of the channels. A surface acoustic wave transducer and at least one surface acoustic wave reflector, or at least two transducers are formed on a surface of the substrate opposite the channels at a portion of the substrate that is thinned by the channels, so that the acoustic tracks of the surface acoustic wave device extend along the channels. The response of the surface acoustic wave depends on the response of the sensor material to a sensed fluid supplied to the channels.

Although other modifications and changes may be suggested by those skilled in the art, it is the intention of the inventors to embody within the patent warranted hereon all changes and modifications as reasonably and properly come within the scope of their contribution to the art.

What is claimed is:

1. An acoustic wave array sensor device, comprising
   (a) a single crystal piezoelectric substrate;
   (b) said single crystal piezoelectric substrate defining at least two microfluidic channels extending into said substrate at a first side of said substrate so that said single crystal piezoelectric substrate is thinned at said channels to form thinned portions;
   (c) a layer of at least one material with a shear acoustic wave speed lower than a shear acoustic wave speed in said substrate, said layer being deposited on at least a portion of each of said thinned portions at a bottom of said at least two microfluidic channels to provide guiding of an acoustic wave and conversion into a layer guided shear horizontal acoustic plate mode;
   (d) at least one first surface acoustic wave transducer disposed on at least a portion of each said thinned portions, said at least one transducer being disposed on a surface of said piezoelectric substrate at a second side opposite from said first side;

(e) at least one second surface acoustic wave element formed on a portion of each of said thinned portions on said second side of said substrate, said at least one second acoustic wave element being spaced from said at least one first surface acoustic wave transducer; and (f) wherein the said first surface acoustic wave transducer and said at least one second surface acoustic wave element in each channel are structured so as to effect uniquely identifiable responses from each channel.

2. An acoustic wave array sensor device as defined in claim 1, wherein said layer of at least one material includes at least two mutually different layers in at least two of said microfluidic channels so as to provide both guiding of the wave into a layer guided shear horizontal acoustic plate mode and selective interaction with targets of interest.

3. An acoustic wave array sensor device as defined in claim 2, wherein at least one of said at least two mutually different layers includes a layer including attachment of biological moieties selective for interaction with targets of interest.

4. An acoustic wave array sensor device as defined in claim 2, wherein at least one of said at least two mutually different layers includes a layer that selectively interacts with chemical analytes of interest.

5. An acoustic wave array sensor device as defined in claim 4, wherein the selective interaction for chemical analytes of interest is effected through at least one chemical reaction between said at least one of said at least two mutually different layers and the analyte of interest.

6. An acoustic wave array sensor device as defined in claim 4, wherein the selective interaction for chemical analytes of interest is effected through at least one physical interaction between said at least one of said at least two mutually different layers and the analyte of interest.

7. An acoustic wave array sensor device as defined in claim 2, further comprising: an output capable of producing a signal for use by a pattern recognition device said output being connected to each of said first transducers so that the pattern recognition device can perform an evaluation of a selective interaction of acoustic channels in each device with targets using pattern recognition.

8. An acoustic wave array sensor device as defined in claim 1, wherein at least two of said microfluidic channels are disposed at mutually different orientations relative to a substrate crystal axes so as to provide complementary information from the waves propagating in different directions.

9. An acoustic wave array sensor device as defined in claim 1, wherein said sensor is operable to provide measurement of a physical parameter.

10. An acoustic wave array sensor device as defined in claim 1, further comprising: a sensor package at least partially enclosing said substrate such that a surface of said substrate having said transducers is protected from an environment.

11. An acoustic wave array sensor device as defined in claim 1, further comprising: a lid operable to temporarily cap at least one of said microfluidic channels to provide for coating of said at least one of said microfluidic channels with said at least one layer material.

12. An acoustic wave array sensor device as defined in claim 2, further comprising: a lid operable to temporarily cap at two of said microfluidic channels for selective coating of said microfluidic channels with at least two different layer materials.

13. An acoustic wave array sensor device as defined in claim 1, further comprising: a permanent cap disposed to cover at least one of said microfluidic channels for selective distribution of fluid samples into said microfluidic channels and for disposition of the samples at an outlet of said channels.

14. An acoustic wave array sensor device as defined in claim 13, further comprising: a cover with a common inlet plenum for even distribution of fluid samples into selected ones of said microfluidic channels and for disposition of the samples at an outlet of said channels via at least one of an outlet tube or plenum.

15. An acoustic wave array sensor device as claimed in claim 1, wherein said microfluidic channels are structured by being formed in said substrate by a single sided micromachining process.

* * * * *